Figure 1:
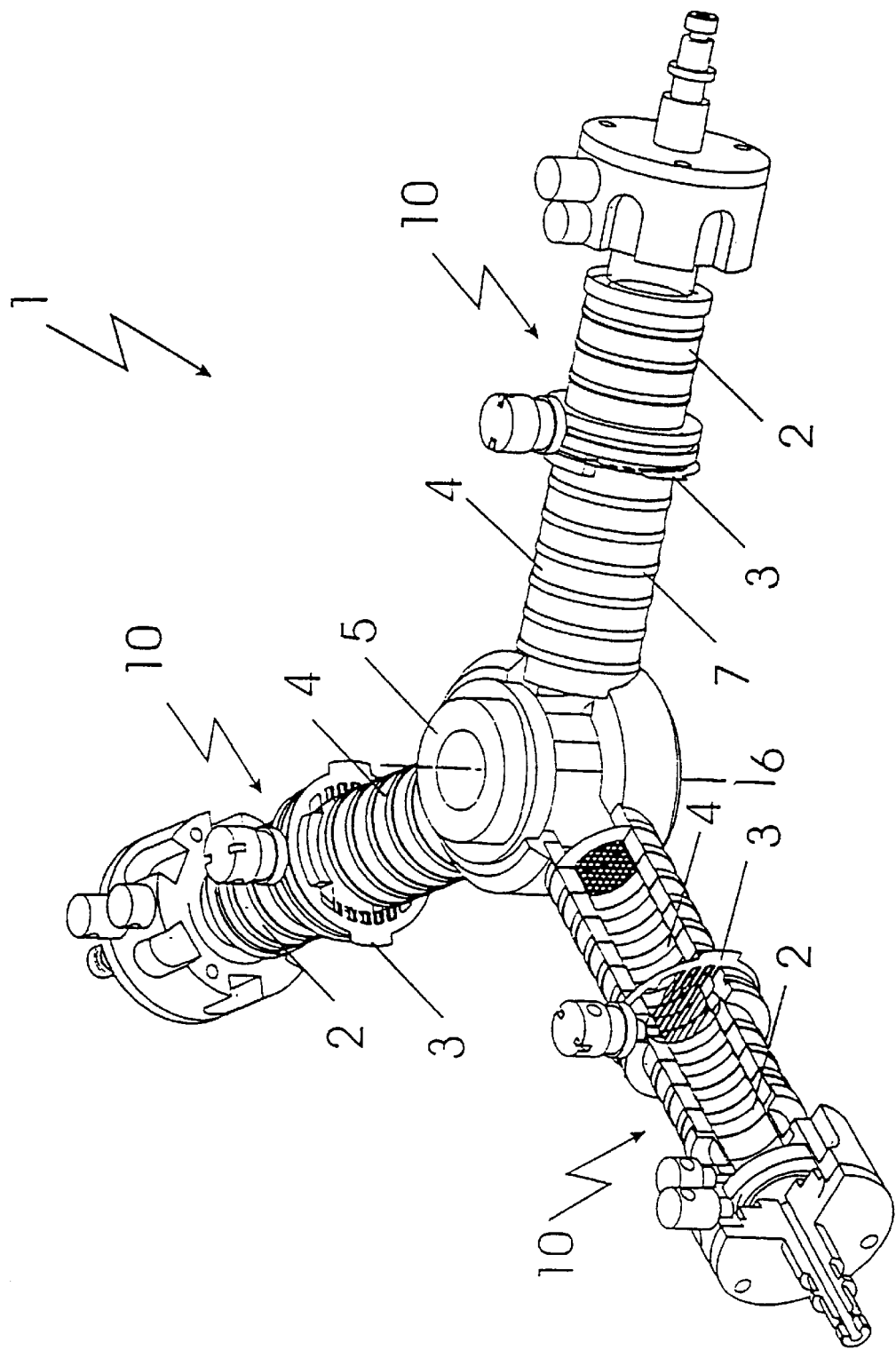

United States Patent
Döring et al.

[11] Patent Number: 6,100,521
[45] Date of Patent: Aug. 8, 2000

[54] ION MOBILITY SPECTROMETER IN A CENTRIPETAL ARRANGEMENT

[75] Inventors: Hans-Rüdiger Döring, Leipzig; Stefan Klepel, Taucha; Jörg Peuker, Leipzig; Roland Schnurpfeil, Bremen; Gerhard Weiss, Weyhe, all of Germany

[73] Assignee: Bruker-Saxonia Analytik GmbH, Leipzig, Germany

[21] Appl. No.: 09/115,370

[22] Filed: Jul. 14, 1998

[30] Foreign Application Priority Data

Jul. 18, 1997 [DE] Germany ............................ 197 30 896

[51] Int. Cl.[7] .................................................... H01J 49/00
[52] U.S. Cl. ........................................... 250/286; 250/287
[58] Field of Search ...................................... 250/286, 287

[56] References Cited

U.S. PATENT DOCUMENTS

| 2,917,628 | 12/1959 | Schwede | 250/286 |
| 4,855,595 | 8/1989 | Blanchard | 250/287 |
| 4,994,748 | 2/1991 | Rasulev et al. | 324/468 |
| 5,227,628 | 7/1993 | Turner | 250/286 |
| 5,256,874 | 10/1993 | Chutjian | 250/286 |
| 5,465,607 | 11/1995 | Corrigan et al. | 250/286 |

FOREIGN PATENT DOCUMENTS

| 2217103 | 10/1989 | United Kingdom . |
| 2228139 | 8/1990 | United Kingdom . |
| 8805535 | 7/1988 | WIPO . |

*Primary Examiner*—Kiet T. Nguyen

[57] ABSTRACT

An ion mobility spectrometer (IMS) with electric drift fields directed at a central detector electrode. The IMS is rotationally symmetrical and has a disk shape.

15 Claims, 2 Drawing Sheets

ION MOBILITY SPECTROMETER IN A CENTRIPETAL ARRANGEMENT

FIELD OF INVENTION

The invention relates to an ion mobility spectrometer (IMS) with at least one ion source, at least one switchable grid, at least one drift chamber, in each of which there is an electric drift field and a collecting electrode, whereby the drift fields are essentially directed radially with respect to an axis or a point.

PRIOR ART

Such an IMS is known from the International Disclosure Statement WO 88/05535 A3, where an IMS is revealed in which the ionization chamber, switchable grid, drift chamber, and collecting electrode essentially demonstrate a rotational symmetry.

Normally IMSs are comprised of an ion source which ionizes molecules of a sample gas within an ionization compartment in the IMS. In most cases the beams of an radioactive emitter are used for ionization. Via a switchable grid, opened periodically in short pulses, ion packages pass into a drift compartment of the IMS, where they are transported by an axial electric field generated by ring electrodes arranged along a tube-shaped drift compartment. Finally, they reach a collecting electrode at the opposite end of the drift compartment, where they generate a current which is amplified and measured. Since heavier ions are less mobile than light ones, they will require a longer drift time. This means the lighter ions from the original ion package arrive first and the heaviest last. After the pulsed opening of the switchable grid, the current is measured at the collecting electrode as a function of time, the current intensity at a given point in time being a measure of the concentration of ions of a specific type. The drift time, with its associated mobility, is then a measure of the respective mass of the ions.

The fundamental design of the IMS and its operation are well known to the specialist and are summarized, for example, in the textbooks "Ion Mobility Spectrometry" by G. A. Eiceman and Z. Karpas (CRC Press, 1994) and "Plasma Chromatography" ed. T. W. Carr (Plenum Press, 1984). Details cannot and will not be repeated here. However, the invention described further below can naturally be used in combination with the known prior art variants of the IMS.

Miniaturization of IMS is highly desirable, but creates the problem that the active surface of the ion source and the volume of the ionization compartment are also reduced with the minification of the linear dimensions of the IMS, which then decreases sensitivity due to the decreased number of ions generated.

The rotational IMS in the paper quoted above initially tries to improve sensitivity as compared to the linear IMS, to be achieved by enlarging the collecting electrode and keeping the ion source unchanged. For this purpose, a cylindrical geometry was selected with an external collecting electrode. One disadvantage, among others, of this IMS is that the electric drift field declines radially toward the outside, meaning that, contrary to established experience, it is weakest directly in front of the collecting electrode, which leads to increased ion losses through diffusion. This IMS is not concerned with the problems of miniaturization and provides no information in this respect.

There is a need for IMS instruments with reduced dimensions but with a level of sensitivity which is either the same or higher then hitherto.

SHORT DESCRIPTION OF THE INVENTION

This problem is solved by locating the collecting electrode ("detector") essentially on a central axis or a central point, directing the drift fields radially towards this detector and maintaining an equal distance for all switchable grids from this detector. The distance between the grids and the detector is smaller than the distance between the ion sources and the detector.

Because the drift fields are directed towards the central detector, the electric field intensity normally increases when approaching the collecting electrode; the disadvantages mentioned in conjunction with the above cited WO 88/05535 A3 are avoided. Even with reduced dimensions, several ion sources can be used simultaneously, or a single expanded source at the periphery of the IMS. In this way, the sensitivity can be maintained or even increased.

Several individual IMSs with their own ion sources, switchable grids and drift compartments can be combined using a common detector, whereby the latter may be designed essentially in the shape of a point, so that the individual drift paths "target" the common detector three-dimensionally in a "star" shape. Here all drift paths are of equal length.

However, it is preferable to arrange the common detector around an axis. Then, too, the individual drift paths may be staggered axially to one another. However, it is especially preferable that they all essentially lie on one plane and be directed at the collecting electrode in a star shape in one plane.

Essentially it is preferable for the IMS to have an n-numbered symmetry relative to an axis where $2 \leq n \leq \infty$. With optimal utilization of the space, this is a simple arrangement to manufacture.

Especially preferable are IMSs for which there are no longer any discrete, individual drift paths, but instead essentially have rotational symmetry relative to an axis. In this way, the individual switchable grids may also be discarded, the design is simplified further and the essentially planar space available is optimally used. For this reason, a single switchable grid should also have essentially rotational symmetry.

Essentially planar or disk-shaped embodiments are especially adapted to the requirements and possibilities of microfabrication technology. Here the axial expansion is much less than the radial expansion, particularly with a ratio less than 1:5.

Advantageously, field-supporting electrodes are provided in the drift compartment(s) to form and stabilize the electric drift fields. In this way, a required electric drift field characteristic can be set and impressed within wide limits within the drift range. In embodiments with separate individual drift paths, the field-supporting electrodes can be designed as standard field support rings or also as a continuous high-resistance coating for the individual drift tubes.

For the rotationally symmetrical embodiments with only one common drift compartment, the field-supporting electrodes are preferably arranged concentrically around the axis. They each consist of two axially staggered rings at equal potential, which determine a defined intermediate ate potential for their respective radial distance from the axis. Through a corresponding high voltage divider, the radial characteristics of the electric drift field can thus be determined and maintained. These defined ratios provide enormous advantages in stability. For example, the arrangement described in WO 88/5535 A3, the current field distribution in the drift compartment there (between R1 and R3) is poorly defined and will be greatly distorted by the charges in the drifting ion cloud.

The field-supporting electrodes in a rotationally symmetric IMS may also have the form of two spirals from highly resistive material, saving the high-voltage divider.

SHORT DESCRIPTION OF THE FIGURES

Figure 2:
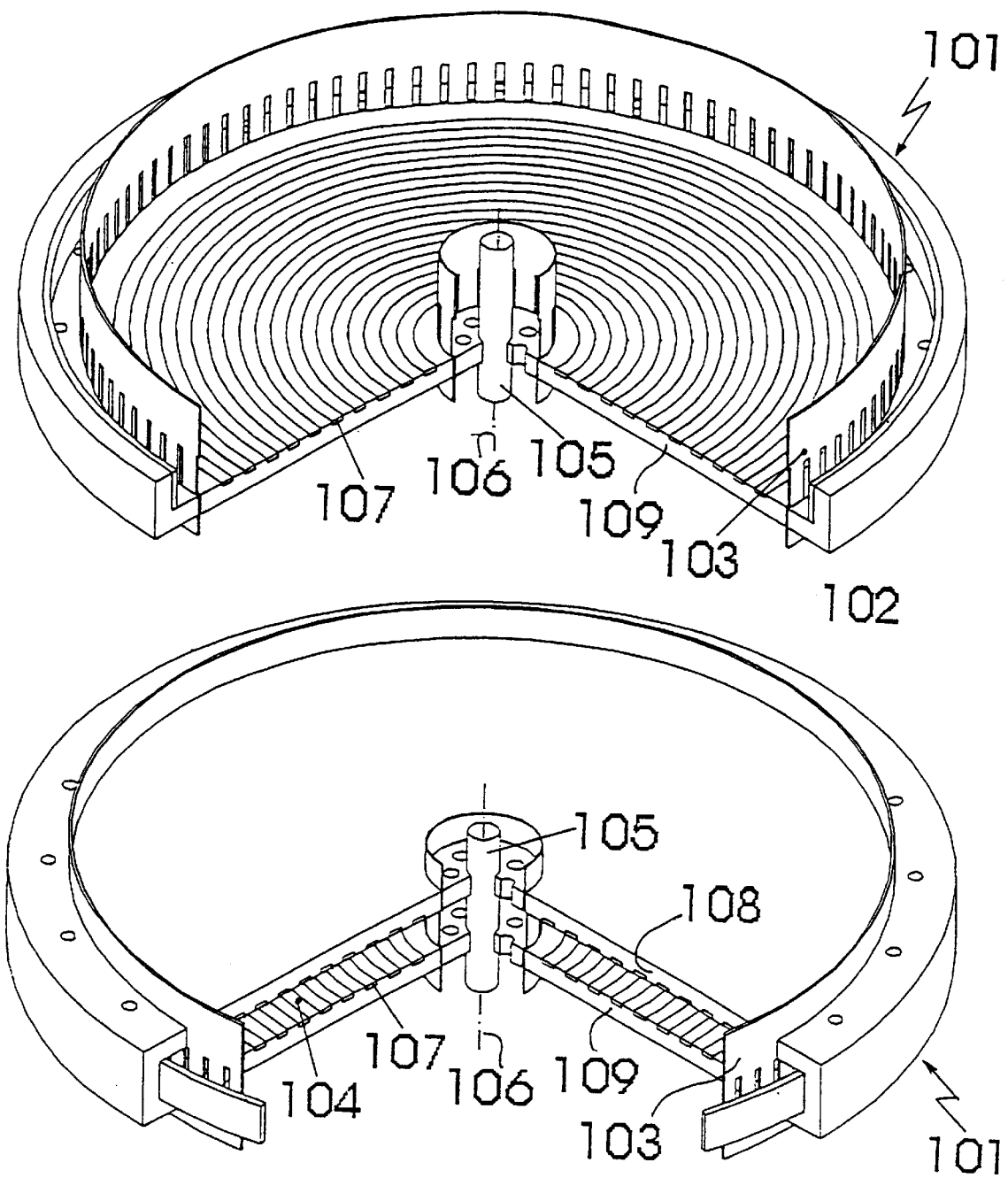

FIG. 1: Three-dimensional, partially cut-away drawing of a first embodiment of an ion mobility spectrometer according to the invention;

FIG. 2: Three-dimensional, partially cut-away drawing of a second embodiment of an ion mobility spectrometer according to the invention; above: with the top plate raised.

EMBODIMENTS

In one version of embodiment of the invention, several different ion sources can be provided simultanously. In this way, the range of substances which can be detected may be increased. Even with different sources, the lengths of the individual drift paths would nevertheless still be identical. Possible sources are radioactive alpha and beta emitters, corona discharges or irradiation with VUV lamps.

In an alternative embodiment, a large number of identical ion sources can be provided. In this way, the sensitivity may be increased essentially in proportion to the number of the sources.

In another embodiment, a single ion source with rotational symmetry is provided, from which the drift path reaches centripetally from a rotationally symmetrical switchable grid towards the central collecting electrode.

The source can be, for example, a radioactive emitter arranged like a ribbon, or, as a non-radioactive source, a circular insulated corona wire at high voltage. It is also possible to use a surface ionization source, such as is described in U.S. Pat. No. 4,994,748 with a ribbon-shaped design.

Preferably, at least one ion source is a radioactive source. Radioactivity ion sources require no external energy.

In an especially favorable embodiment, the IMS essentially has a disk shape with top and bottom plates aligned at right angles to the axis, manufactured using methods from microfabrication technology. This design is especially suitable for miniaturization and for integration in miniaturized apparatuses.

Naturally the characteristics described above and further below need not be used only in the respective combination mentioned but also in any other combination or alone, without leaving the scope of the invention.

The invention is explained more closely using examples of embodiments shown in the drawing.

Specifically, FIG. 1 shows an IMS 10 with a collecting electrode 5, which directly surrounds an axis 6. With a very short overall length for the axis, the collecting electrode 5 may also be viewed as "point-shaped." It then defines a symmetrical center for the arrangement. Pointing to the central detector electrode 5 in the embodiment example, three separate identical measuring cells 10, arranged essentially in a plane at right angles to the axis 6, staggered at 120°, each consisting of a drift compartment 4 with field support rings 7, a switchable grid 3 and an ion source 2.

In other embodiments, the number of measuring cells can vary, they also need not be arranged in one plane but instead can form a three-dimensional star aimed towards the essentially point-shaped detecting electrode. The arrangement can also deviate from the axial symmetry, i.e. the measuring cells can enclose any angle in the plane. For an axially expanded detector electrode, the measuring cells can also be staggered axially to one another.

The ion sources 2 on the embodiment example can be identical. They are then preferably operated in parallel at the same time, i.e. all switchable grids 3 are opened and closed synchronously.

The ion sources 2 in the embodiment example can however also be different. They are then preferably operated one after another temporally, i.e. the switchable grids 3 for the various measuring cells are opened and closed while staggered in time, since the spectra attained with the various measuring cells contain varying information.

FIG. 2 shows a further embodiment example of the invention, whereby the IMS 101 has an approximate disk shape. The individual measuring cells in FIG. 1 are incorporated into a single, rotationally symmetrical one. At the center of the arrangement, a detector 105 again surrounds the symmetrical axis 106 of the unit. The single drift compartment 104 is shaped like a very short hollow cylinder. On the inside of its top 108 and bottom surface 109, concentric field-shaping rings 107 are attached in the form of ring pairs, whereby corresponding rings are at the same potential on the top 108 and bottom plate 109. The drift compartment 104 is limited radially toward the outside by a rotationally symmetrical switchable grid 103 or by a series of many switchable grids, arranged in a circular cylinder, which nevertheless is always at the same potential, i.e. it is operated synchronously. Radially outside the switchable grid 103 is a rotationally symmetrical ion source 102. Analogous to the switchable grid 103, it can be also replaced by an arrangement of identical single sources. Without the field-shaped rings 107, the electric field in drift compartment 104 would approximately decline as $1/r^2$. Due to the field-shaped rings 107, a sufficiently constant electric radial field can be generated nevertheless in drift compartment 104. Generally, by adjusting the potentials on the ring pairs 107, almost any required potential characteristic can be adjusted between the limit potentials. The field-shaped ring pairs 107 can also be replaced by a corresponding continuous high-resistance coating on the top 108 and bottom surface 109. The coatings are preferably homogeneous, although they may also be textured, whereby rotational symmetry is nevertheless maintained.

What is claimed is:

1. Ion mobility spectrometer (IMS) having a center and comprising (a) at least one ion source, (b) a plurality of switchable grids each controlling a separate group of ions, (c) a detector electrode located in the center of the IMS, substantially equidistant to each of the switchable grids, and (d) a plurality of drift compartments with electric drift fields of each drift compartment directed radially towards the detector electrode.

2. IMS as in claim 1, wherein the IMS has substantially an n-fold symmetry relative to an axis through said center with n ion sources and n grids, where $2 \leq n \leq \infty$.

3. IMS as in claim 1, wherein the IMS substantially has rotational symmetry relative to an axis through the center.

4. IMS as in claim 3, wherein the drift compartment substantially has rotational symmetry.

5. IMS as in claim 4, wherein the switchable grid substantially has rotational symmetry.

6. IMS as in claim 3, wherein an axial dimension of the IMS is much smaller than a radial dimension of the IMS.

7. IMS as in claim 6, wherein said axial dimension is smaller than said radial dimension by a ratio of less than 1:5.

8. IMS as in claim 3, wherein a rotationally symmetrical ion source is provided.

9. IMS as in claim 3, wherein the IMS has a disk shape with top and bottom plates which are aligned substantially at right angles to the axis and are manufactured using methods of microfabrication technology.

10. IMS as in claim 3, wherein field-supporting electrodes are provided having the form of concentric pairs of rings.

11. IMS as in claim 3, wherein field-supporting electrodes are provided having the form of flat spirals made out of highly resistive material.

12. IMS as in claim 1, wherein field-supporting electrodes are provided in the drift compartments to form and stabilize the electric drift field.

13. IMS as in claim 1, wherein several different ion sources are provided.

14. IMS as in claim 1, wherein a number of identical ion sources are provided.

15. IMS as in claim 1, wherein at least one ion source is a radioactive ion source.

* * * * *